(12) United States Patent
Kaouas et al.

(10) Patent No.: US 8,470,384 B2
(45) Date of Patent: Jun. 25, 2013

(54) OXALAMIDE DERIVATIVE AS UMAMI FLAVOURING AGENT

(75) Inventors: Abdelmajid Kaouas, Utrecht (NL); Cornelis Winkel, Bussum (NL)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 13/576,572

(22) PCT Filed: Feb. 3, 2011

(86) PCT No.: PCT/EP2011/051528
§ 371 (c)(1), (2), (4) Date: Aug. 1, 2012

(87) PCT Pub. No.: WO2011/095533
PCT Pub. Date: Aug. 11, 2011

(65) Prior Publication Data
US 2012/0301587 A1   Nov. 29, 2012

(30) Foreign Application Priority Data

Feb. 4, 2010 (GB) .................................... 1001796.0

(51) Int. Cl.
*A23L 1/226* (2006.01)
*C07D 213/56* (2006.01)

(52) U.S. Cl.
USPC ........................................ 426/537; 546/336

(58) Field of Classification Search
USPC ........................................................ 426/537
See application file for complete search history.

(56) References Cited

U.S. PATENT DOCUMENTS

| | | | |
|---|---|---|---|
| 7,175,872 B2 | 2/2007 | Hofmann et al. | |
| 7,541,055 B2 | 6/2009 | Dewis et al. | |
| 2004/0171648 A1 | 9/2004 | Hofmann et al. | |
| 2005/0084506 A1 | 4/2005 | Tachdjian et al. | |
| 2006/0045953 A1 | 3/2006 | Tachdjian et al. | |
| 2006/0068071 A1 | 3/2006 | Dewis et al. | |
| 2007/0104709 A1 | 5/2007 | Li et al. | |
| 2007/0161053 A1 | 7/2007 | Li et al. | |
| 2008/0085994 A1 | 4/2008 | Li et al. | |
| 2009/0111834 A1 | 4/2009 | Tachdjian et al. | |
| 2009/0280230 A1 | 11/2009 | Shigemura et al. | |
| 2010/0080880 A1 | 4/2010 | Backes et al. | |
| 2011/0223618 A1 | 9/2011 | Li et al. | |
| 2011/0294981 A1 | 12/2011 | Li et al. | |

FOREIGN PATENT DOCUMENTS

| | | |
|---|---|---|
| EP | 1 291 342 A | 3/2003 |
| EP | 1 312 268 A1 | 5/2003 |
| EP | 1 473 287 A2 | 11/2004 |
| EP | 1 642 886 A2 | 4/2008 |
| EP | 2 168 442 A2 | 3/2010 |
| WO | WO 03/088768 A1 | 10/2003 |
| WO | WO 2005/015158 A2 | 2/2005 |
| WO | WO 2006/003107 A1 | 1/2006 |
| WO | WO 2006/084246 A2 | 8/2006 |
| WO | WO 2007/124152 A2 | 11/2007 |

OTHER PUBLICATIONS

PCT/EP2011/051528—International Preliminary Report on Patentability, Aug. 8, 2012.
PCT/EP2011/051528—International Search Report, Mar. 22, 2011.
PCT/EP2011/051528—International Written Opinion, Mar. 20, 2011.
GB 1001796.0—Search Report, May 26, 2010.
Yamaguchi, S., et al., "What is Umami?", Food Reviews International, 1998, vol. 14, pp. 123-138.

*Primary Examiner* — Nikki H Dees
(74) *Attorney, Agent, or Firm* — Curatolo Sidoti Co., LPA; Joseph G. Curatolo; Salvatore A. Sidoti

(57) ABSTRACT

The compound of the formula (1)

(1)

is novel and is useful in conferring umami taste on consumable compositions, such as foodstuffs and beverages.

21 Claims, No Drawings

OXALAMIDE DERIVATIVE AS UMAMI FLAVOURING AGENT

CROSS REFERENCE TO RELATED APPLICATIONS

This application is a national stage application of International Application No. PCT/EP2011/051528, filed 3 Feb. 2011, which claims priority from Great Britain Patent Application No. 1001796.0, filed 4 Feb. 2010, from which applications priority is claimed, and which are incorporated herein by reference.

This disclosure relates to a novel molecule and its use in creating umami flavour.

Umami is a flavour sensation generally associated with Asian cuisine. In addition, improved umami taste helps make low salt products more palatable. Umami flavour has traditionally been achieved by the addition of monosodium glutamate (MSG) to foodstuffs. However, the presence of MSG in foodstuffs is not universally welcome, and there is an interest in the achievement of umami taste with lower proportions of MSG than is normally the case.

It has now been found that it is possible to achieve umami taste with a reduced proportion of MSG, or even the complete elimination of umami. This is achieved by means of a novel compound. There is therefore provided a compound of the formula (1)

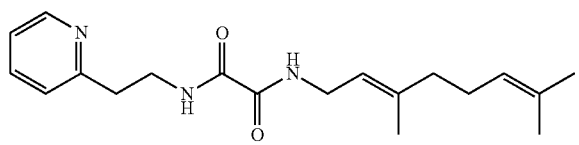

(1)

There is further provided a umami flavour composition, comprising flavour ingredients and a umami-enhancing or -providing proportion of a compound of the formula (1).

There is further provided a consumable composition having umami flavour, said umami flavour being at least partially provided by the presence therein of a compound of the formula (1).

There is further provided a method of conferring umami flavour on a consumable composition, comprising the addition to the composition of a compound of the formula (1).

The compound of formula (1) (hereinafter referred to as "the Umami Compound") exists in two isomeric forms, the E-form and the Z-form. Both of these compounds are comprehended by the formula (1), and both may be used, either in pure form or in a mixture of isomers. The E-form is N1-neryl-N2-(2-(pyridin-2-yl)ethyl)oxalamide and the Z-form N1-geranyl-N2-(2-(pyridin-2-yl)ethyl)oxalamide.

The Umami Compound may be prepared by methods well known to the art. One such method involves the preparation of (E)-ethyl-2-(3,7-dimethylocta-2,6-dienylamino-2-oxoacetate

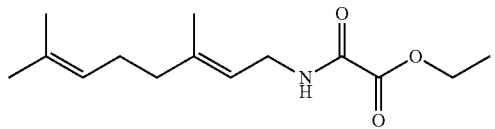 [SMILES: CCOC(=O)C(=O)NC/C=C(\C)CCC=C(C)C]

by reaction of geranylamine with diethyl oxalate. This product is then reacted with 2-(pyridin-2-yl)ethanamine. Precise details are set forth in the examples.

It has been surprisingly found that the Umami Compound not only confers a high degree of umami flavour and at very low dosages, but also that this flavour is of unusual quality, in that it has a clean, non-artificial taste. This is in contrast to many other non-MSG umami flavourants.

The Umami Compound may be used alone, or it may be mixed with other flavouring ingredients to provide a flavouring composition ready for addition to a consumable composition. The flavouring ingredients may include other umami flavourants, including MSG. Use of the Umami Compound allows a considerable reduction in MSG levels, and in some cases the complete elimination of MSG.

Particular examples of other umami compounds that are useful in this application are compounds (including salts thereof) according to Formula (2)

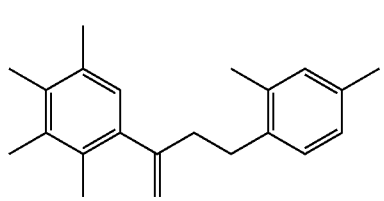

(2)

in which
$R^1$ is selected from H, methyl and ethyl;
$R^2$ is selected from H, OH, fluorine, $C_1$-$C_4$ linear or branched alkyl, $C_1$-$C_6$ alkoxy wherein the alkyl group is linear or branched, or comprises or consists of a $C_3$-$C_5$ cycloalkyl moiety;
$R^3$ is selected from H and methoxy;
or $R^2$ and $R^3$ together form a bridging moiety —O—$CH_2$—O— between the phenyl carbon atoms to which they are connected;
$R^4$ is selected from OH and methoxy; and
$R^5$ and $R^6$ are independently selected from H and methyl;
$R^1$, $R^2$, $R^3$, $R^4$, $R^5$ and $R^6$ being selected such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and
(ii) when $R^4$ is OH and $R^1$-$R^3$ are H, at least one of $R^5$, $R^6$ is methyl.

In a particular embodiment, $R^2$ is selected from H, OH, fluorine, methyl, $C_1$-$C_6$ alkoxy wherein the alkyl group is linear or branched, or comprises or consists of a $C_3$-$C_5$ cycloalkyl moiety.

In a further particular embodiment, $R^2$ is selected from methyl, methoxy and isobutyloxy. $R^3$ is H, $R^4$ is OH and $R^5$ and $R^6$ are H.

Such compounds are described in UK patent application No. 0913804. Particular non-limiting examples of such compounds include:
1-(2-hydroxy-4,5-dimethylphenyl)-3-(pyridine-2-yl)propan-1-one;
1-(2-hydroxy-4-methylphenyl)-3-(pyridin-2-yl)propan-1-one;
1-(2-hydroxy-4-methoxyphenyl)-3-(pyridin-2-yl)propan-1-one;
1-(2-hydroxy-4-isobutoxyphenyl)-3-(pyridine-2-yl)propan-1-one.

Other non-limiting examples of suitable compounds include:

N1-(2-methoxy-4-methylbenzyl)-N2-(2-pyridin-2-yl-ethyl) oxalamide;

N1-(2,4-dimethoxybenzyl)-N2-(2-pyridin-2-yl-ethyl)oxalamide;

N1-(2-methoxy-3-methylbenzyl)-N2-(2-(−5-methyl)pyridin-2-yl-ethyl)oxalamide;

N-heptan-4-yl benzo(D)-1,3-dioxole 5-caboxamide;

N(3,7-dimethyl-2,6-octadien-1-yl)cyclopropyl carboxamide;

cyclopropane carboxylic acid 2-isopropyl-5-methyl-cyclohexyl amide.

Other non-limiting examples of umami flavour-conferring and -enhancing compounds that may be used with the Umami Compound include those described in EP 1642886, WO 2005/015158, EP 1312268, WO 2003/088768, EP 1291342 and WO 2006/003107.

The proportion of the Umami Compound used will depend on the nature of the use and the effect desired. For example, the proportion needed for a partial replacement of MSG will naturally be lower than that of a complete MSG replacement. The proportion may vary between wide limits, typically between 0.1 ppm and 10 ppm by weight of a consumable composition, more particularly between 0.5 ppm and 5 ppm. However, these are general indications only of useful proportions, and the skilled flavourist may use proportions outside these ranges for particular effects.

By "consumable composition" is meant any composition that is taken into the mouth for ultimate spitting out or ingestion. The composition may be in any physical form, solid, liquid or gaseous. Non-limiting examples include all food products, food additives, nutraceuticals, pharmaceuticals and any product placed in the mouth including (but not limited to) chewing gum, oral care products, and oral hygiene products including but not limited to, cereal products, rice products, tapioca products, sago products, baker's products, biscuit products, pastry products, bread products, confectionery products, dessert products, gums, chewing gums, flavor or flavor-coated food/beverage containers, yeast products, baking-powder, salt and spice products, snack foods, savoury products, mustard products, vinegar products, sauces (condiments), soups, seasonings, ready-to-eat meals, gravies, nuts & nut products, processed foods, vegetable products, meat and meat products, egg products, milk and dairy products, yoghurts, cheese products, butter and butter substitute products, milk substitute products, soy products, edible oils and fat products, beverages, carbonated beverages, alcoholic drinks such as beers, wines and spirits, non-alcoholic drinks such as soft drinks, including forms requiring reconstitution including, without limitation, beverage powder, milk based beverage powder, sugar-free beverage powder, beverage syrup, beverage concentrate, coffee and tea, food extracts, plant extracts, meat extracts, condiments, gelatins, pharmaceutical and non-pharmaceutical gums, tablets, lozenges, drops, emulsions, elixirs, syrups and other preparations for making beverages, and combinations thereof.

The disclosure is further described with reference to the following non-limiting examples, which depict particular embodiments.

EXAMPLE 1

Preparation procedure for N1-geranyl-N2-(2-(pyridin-2-yl)ethyl)oxalamide

Step 1: preparation of (E)-ethyl-2-(3,7-dimethylocta-2,6-dienylamino-2-oxoacetate

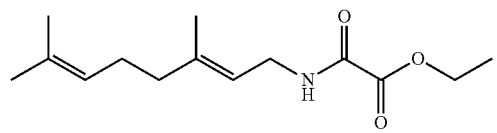 [SMILES: CCOC(=O)C(=O)NC/C=C(\C)CCC=C(C)C]

Geranylamine (5 g, 32.6 mmol) was added dropwise to diethyl oxalate (15 g, 103 mmol) to give a colorless solution. The solution was heated to 12° C. and stirred at this temperature for 2 hours; the formed ethanol was distilled off during the reaction. The excess of diethyl oxalate was removed by vacuum distillation until 160° C./lmbar. 8.1 g (93% yield) of brownish residual oil was obtained. The product is ca. 95% pure according to NMR analysis $^1$H-NMR in CDCl$_3$ (ppm): 1.26-1.41 (3H, t, COOCH2-CH3), 1.60 (3H, s, CH2-C(CH3)=CH—), 1.68 (6H, s, (CH3)$_2$-C=CH—), 2.01 (2H, m, —CH2-CH2-C(CH3)=CH—), 2.08 (2H, m, (CH3)$_2$-C=CH—CH2-CH2), 3.89 (2H, t, CH2-C(CH3)=CH—CH2-NH—), 4.22-4.38 (2H, q, COOCH2-CH3) 5.07 (1H, m, (CH3)$_2$-C=CH—CH2-), 5.20 (1H, m, CH2-C(CH3)=CH—CH2-NH—), 7.37 (1H, s, CONH—CH2-CH=C(CH3)-CH2)

Step 2: preparation of N1-geranyl-N2-(2-(pyridin-2-yl)ethyl)oxalamide

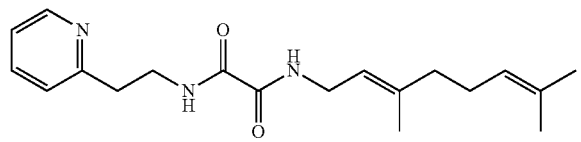 [SMILES: CC(C)=CCC/C(C)=C/CNC(=O)C(=O)NCCc1ccccn1]

The ethyl 2-(3,7-dimethylocta-2,6-dienylamino)-2-oxoacetate (1.5 g, 5.92 mmol) was mixed with 2-(pyridin-2-yl) ethanamine (1 g, 8.19 mmol) in ethanol (20 ml) to give a yellow solution. The reaction mixture was stirred at reflux for 1.5 hour. Then the solvent was removed by evaporation. The remaining residual solid was washed with ethanol/pentane to provide the target compound as white crystals (1.3 g; 65% yield). The product is ca. 97% pure according to NMR analysis.

$^1$H-NMR in CDCl$_3$ (ppm): 1.60 (3H, s, CH2-C(CH3)=CH—), 1.68 (6H, s, (CH3)$_2$-C=CH—), 2.01 (2H, m, —CH2-CH2-C(CH3)=CH—), 2.08 (2H, m, (CH3)$_2$-C=CH—CH2-CH2), 3.04 (2H, t, NH—CH2-CH2-pyridinyl), 3.89 (2H, t, CH2-C(CH3)=CH—CH2-NH—), 3.76 (2H, q, NH—CH2-CH2-pyridinyl), 5.07 (1H, m, (CH3)$_2$-C=CH—CH2-), 5.20 (1H, m, CH2-C(CH3)=CH—CH2-NH—), 7.14-7.16 (2H, m, 2×CH from pyridinyl), 7.37 (1H, s, CONH—CH2-CH=C(CH3)-CH2), 7.61 (1H, t, CH from pyridinyl), 8.15 (1H, s, CONH—CH2-CH2-pyridinyl), 8.57 (1H, m, CH from pyridinyl)

EXAMPLE 2

Testing of Compound

Two solutions were prepared:
A—a solution of 0.3% NaCl and 0.05% MSG
B—a solution of 0.3% NaCl and 3 ppm of N1-geranyl-N2-(2-(pyridin-2-yl)ethyl)oxalamide.

The samples were tasted by a professional panel composed of 2 women and 3 men aged between 30 and 60. The panel agreed that both solutions tasted umami. They also agreed that solution B was slightly stronger umami, had more succulence and sweetness and had more lingering savoury notes.

EXAMPLE 3

Testing of Compound

Two solutions were prepared:
A—a solution of 0.5% NaCl, 0.15% MSG and 0.025% Ribonucleotide mixture
B—a solution of 0.5% NaCl, 0.05% MSG, 0.010% Ribonucleotide mixture and 1.5 ppm of N1-geranyl-N2-(2-(pyridin-2-yl)ethyl)oxalamide.

The samples were tasted by a professional panel composed of 2 women and 3 men aged between 30 and 60. The panel agreed that both solutions were of equal umami strength.

The invention claimed is:

1. A compound of the formula (1)

(1)

2. The compound N1-neryl-N2-(2-(pyridin-2-yl)ethyl)oxalamide.

3. The compound N1-geranyl-N2-(2-(pyridin-2-yl)ethyl)oxalamide.

4. A umami flavour composition, comprising flavour ingredients and a umami-enhancing or -providing amount of the compound according to claim 1.

5. The umami flavour composition according to claim 4, in which the flavour composition additionally comprises at least one compound (including salts thereof) according to the Formula (2)

(2)

in which
$R^1$ is selected from H, methyl and ethyl;
$R^2$ is selected from H, OH, fluorine, $C_1$-$C_4$ linear or branched alkyl, and $C_1$-$C_6$ alkoxy wherein the alkyl group is linear or branched, or comprises or consists of a $C_3$-$C_5$ cycloalkyl moiety;
$R^3$ is selected from H and methoxy;
or $R^2$ and $R^3$ together form a bridging moiety —O—$CH_2$—O— between the phenyl carbon atoms to which they are connected;
$R^4$ is selected from OH and methoxy; and
$R^5$ and $R^6$ are independently selected from H and methyl;
$R^1$, $R^2$, $R^3$, $R^4$, $R^5$ and $R^6$ being selected such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and
(ii) when $R^4$ is OH and $R^1$-$R^3$ are H, at least one of $R^5$, or $R^6$ is methyl.

6. A consumable composition having umami flavour, said consumable composition comprising the compound according to claim 1.

7. The consumable composition according to claim 6, comprising the compound in an amount ranging from 0.1 ppm to 10 ppm by weight of the consumable composition.

8. A method of conferring umami flavour on a consumable composition, comprising the addition to the consumable composition of the compound according to claim 1.

9. The method according to claim 8, in which the compound is present in an amount ranging from 0.1 ppm to 10 ppm by weight of the consumable composition.

10. A umami flavour composition, comprising flavour ingredients and a umami-enhancing or -providing amount of the compound according to claim 2.

11. The umami flavour composition according to claim 10, in which the flavour composition additionally comprises at least one compound (including salts thereof) according to the Formula (2)

(2)

in which
$R^1$ is selected from H, methyl and ethyl;
$R^2$ is selected from H, OH, fluorine, $C_1$-$C_4$ linear or branched alkyl, and $C_1$-$C_6$ alkoxy wherein the alkyl group is linear or branched, or comprises or consists of a $C_3$-$C_5$ cycloalkyl moiety;
$R^3$ is selected from H and methoxy;
or $R^2$ and $R^3$ together form a bridging moiety —O—$CH_2$—O— between the phenyl carbon atoms to which they are connected;
$R^4$ is selected from OH and methoxy; and
$R^5$ and $R^6$ are independently selected from H and methyl;
$R^1$, $R^2$, $R^3$, $R^4$, $R^5$ and $R^6$ being selected such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and (ii) when $R^4$ is OH and $R^1$-$R^3$ are H, at least one of $R^5$ or $R^6$ is methyl.

12. A consumable composition having umami flavour, said consumable composition comprising the compound according to claim 2.

13. The consumable composition according to claim 12, comprising the compound in an amount ranging from 0.1 ppm to 10 ppm by weight of the consumable composition.

14. A method of conferring umami flavour on a consumable composition, comprising the addition to the consumable composition of the compound according to claim 2.

15. The method according to claim 14, in which the compound is present in an amount ranging from 0.1 ppm to 10 ppm by weight of the consumable composition.

16. A umami flavour composition, comprising flavour ingredients and a umami-enhancing or -providing amount of the compound according to claim 3.

17. The umami flavour composition according to claim 16, in which the flavour composition additionally comprises at least one compound (including salts thereof) according to the Formula (2)

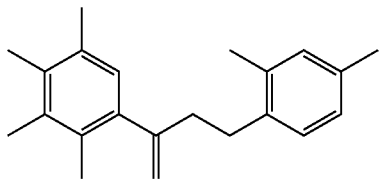

(2)

in which $R^1$ is selected from H, methyl and ethyl;

$R^2$ is selected from H, OH, fluorine, $C_1$-$C_4$ linear or branched alkyl, and $C_1$-$C_6$ alkoxy wherein the alkyl group is linear or branched, or comprises or consists of a $C_3$-$C_5$ cycloalkyl moiety:

$R^3$ is selected from H and methoxy;

or $R^2$ and $R^3$ together form a bridging moiety —O—CH$_2$—O— between the phenyl carbon atoms to which they are connected;

$R^4$ is selected from OH and methoxy; and $R^5$ and $R^6$ are independently selected from H and methyl;

$R^1$, $R^2$, $R^3$, $R^4$, $R^5$ and $R^6$ being selected such that, (i) when $R^2$ and $R^3$ together form a bridging moiety —O—CH$_2$—O— between the phenyl carbon atoms to which they are connected, $R^1$, $R^5$, $R^6$ are H, and $R^4$ is OH; and (ii) when $R^4$ is OH and $R^1$-$R^3$ are H, at least one of $R^5$ or $R^6$ is methyl.

18. A consumable composition having umami flavour, said consumable composition comprising the compound according to claim 3.

19. The consumable composition according to claim 18, comprising the compound in an amount ranging from 0.1 ppm to 10 ppm by weight of the consumable composition.

20. A method of conferring umami flavour on a consumable composition, comprising the addition to the consumable composition of the compound according to claim 3.

21. The method according to claim 20, in which the compound is present in an amount ranging from 0.1 ppm to 10 ppm by weight of the consumable composition.

* * * * *

UNITED STATES PATENT AND TRADEMARK OFFICE
CERTIFICATE OF CORRECTION

PATENT NO.         : 8,470,384 B2
APPLICATION NO.    : 13/576572
DATED              : June 25, 2013
INVENTOR(S)        : Kaouas et al.

It is certified that error appears in the above-identified patent and that said Letters Patent is hereby corrected as shown below:

In the Specifications, in column 2, lines 20-30 and in the Claims, column 5, claim 5; column 6, claim 11, and column 7, claim 17: formula (2) is incorrect. Formula (2) should read:

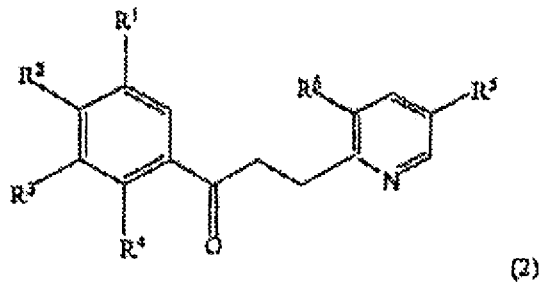

Signed and Sealed this
Thirteenth Day of August, 2013

Teresa Stanek Rea
*Acting Director of the United States Patent and Trademark Office*